United States Patent [19]

Harada et al.

[11] Patent Number: 4,587,214

[45] Date of Patent: May 6, 1986

[54] PROCESS FOR PREPARATION OF ASPARTYLPHENYLALANINE ALKYL ESTERS

[75] Inventors: Tuneo Harada; Hisao Takemoto, both of Shinnanyo; Tatsuo Igarashi, Tokuyama, all of Japan

[73] Assignee: Toyo Soda Manufacturing Co., Ltd., Shinnanyo, Japan

[21] Appl. No.: 520,129

[22] Filed: Aug. 3, 1983

[30] Foreign Application Priority Data

Aug. 6, 1982 [JP] Japan ................................. 57-136332

[51] Int. Cl.$^4$ ........................ C12P 21/00; C12P 21/02; C12N 9/52; C12R 1/40
[52] U.S. Cl. ........................................ 435/70; 435/68; 435/220; 435/874; 435/877; 435/253
[58] Field of Search ................... 435/68, 70, 220, 875, 435/876, 877, 253

[56] References Cited

U.S. PATENT DOCUMENTS 4,256,836 3/1981 Isowa et al. ............................ 435/70
4,335,205 6/1982 Greenwood ........................... 435/37

FOREIGN PATENT DOCUMENTS 0019051 2/1980 Japan ..................................... 435/68

OTHER PUBLICATIONS

Morrison and Boyd *Organic Chemistry*, 1973, Allan & Bacon Inc., p. 870.

*Primary Examiner*—Thomas G. Wiseman
*Assistant Examiner*—Robin Lyn Teskin
*Attorney, Agent, or Firm*—Cushman, Darby & Cushman

[57] ABSTRACT

α-L-aspartylphenylalanine lower alkyl esters are prepared by a process wherein fumaric acid, ammonia and a lower alkyl ester of L-phenylalanine are contacted with a culture or treated culture of a microorganism belonging to the genus Pseudomonas, and being capable of producing a α-L-aspartyl-L-phenylalanine lower alkyl ester from fumaric acid, ammonia and a lower alkyl ester of L-phenylalanine.

12 Claims, No Drawings

PROCESS FOR PREPARATION OF ASPARTYLPHENYLALANINE ALKYL ESTERS

BACKGROUND OF THE INVENTION (1) Field of the Invention

This invention relates to a process for the preparation of aspartylphenylalanine alkyl esters. More particularly, it relates to a process for preparing an α-L-aspartyl-L-phenylalanine lower alkyl ester from fumaric acid, ammonia and an L-phenylalanine lower alkyl ester by utilizing a microorganism.

(2) Description of the Prior Art

An α-L-aspartyl-L-phenylalanine lower alkyl ester (hereinafter referred to as "α-APE" for brevity), especially an α-L-aspartyl-L-phenylalanine methyl ester, is a valuable substance as a novel sweetening agent.

Several processes for the preparation of the α-APE are known. In one process, an N-protected-L-aspartic anhydride is reacted with a lower alkyl ester of L-phenylalanine to form an N-protected-α-APE and then the protecting group is removed to form an α-APE. In another process, an N-protected-L-aspartic acid is reacted with a lower alkyl ester of phenylalanine in the presence of a protease to form an N-protected-α-APE or an adduct of N-protected-α-APE with the lower alkyl ester of phenylalanine, and then, the protecting group is removed to form an α-APE.

The former process has a problem in that an N-protected-β-APE is formed as a by-product together with the N-protected-α-APE. The latter process is advantageous in that the above problem does not rise and a racemic mixture can be used as the starting compound. In each process, however, the starting aspartic acid or its anhydride be used after the amino group has been protected with a protecting group such as a benzyloxycarbonyl group.

If the steps of introducing and removing an amino group-protecting group, which are indispensable in the conventional processes, can be omitted, this will be very advantageous from the industrial viewpoint because the steps of the process are simplified and the loss of the starting and intended compounds is minimized.

SUMMARY OF THE INVENTION

It is therefore a primary object of the present invention to provide a process for preparing an α-APE wherein the intended α-APE can be prepared directly from L-aspartic acid and a lower alkyl ester of L-phenylalanine by simplified process steps.

More specifically, in accordance with the present invention, there is provided a process for the preparation of an aspartylphenylalanine alkyl ester, which comprises contacting a culture or treated culture product of a microorganism belonging to the genus Pseudomonas and being capable of producing an α-L-aspartyl-L-phenylalanine lower alkyl ester from fumaric acid, ammonia and an L-phenylalanine lower alkyl ester, with fumaric acid, ammonia and an L-phenylalanine lower alkyl ester.

DESCRIPTION OF THE PREFERRED EMBODIMENTS

The reaction involved in the process of the present invention can be expressed by the following reaction formula:

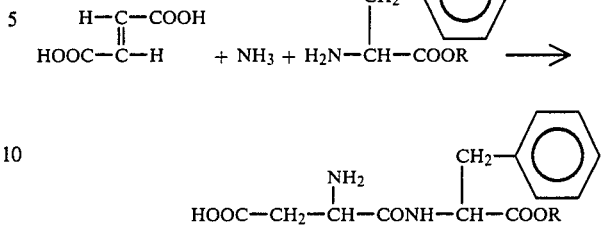

wherein R stands for a lower alkyl group.

The microorganism used in the present invention is an α-APE-producing strain belonging to the genus Pseudomonas. The taxonomical properties of the strain, which has been separated from soil in Shin-Nanyo city, Yamaguchi prefecture, Japan by us, will now be described.

(A) Morphology:

Cultivation on a nutrient broth agar culture medium (after incubation at 37° C. for 6 to 24 hours)

(1) Cell form and cell size: rods, (0.5 to 0.7) μm x (1.0 to 1.5) μm (2) Arrangement: single or pair (3) Motility: motile by polar flagella (4) Endospore: none (5) Gram stainity: negative (6) Acid fastness: negative (B) Cultural characteristics:

(1) Cultivation on a nutrient broth agar plate (after incubation at 37° C. for 2 days)

(a) Colony formation rate: moderate, about 6 mm in diameter (b) Colony form: circular (c) Colony surface: smooth (d) Elevation of growth: convex (e) Edge of colony: entire (f) Content of colony: homogeneous (g) Tint of colony: milky white (h) Transmittance of colony: translucent (i) Glistening of colony: dull (j) Formation of soluble coloring material: soluble light-green pigment formed (2) Cultivation on a nutrient broth agar slant (after incubation at 37° C. for 2 days)

(a) Growth: good (b) Colony form: smooth (c) Elevation of growth: flat (d) Glistening of colony: dull (e) Colony surface: smooth (f) Transmittance of colony: translucent (g) Tint of colony: milky white (h) Content of colony: butyrous (3) Cultivation on a nutrient broth medium (after incubation at 37° C. for 2 days)

(a) Growth on surface: none (b) Turbidity: moderately turbid (c) Precipitate formation: powdery (d) Generation of gas: negative (e) Coloration of medium: negative (4) Cultivation on a nutrient broth agar stab (after incubation at 37° C. for 2 days)

(a) Location of growth: uniform (b) Form of colony: papillate (5) Cultivation on a nutrient broth gelatin stab (after inculation at 20° C. for 14 days)

(a) Liquefaction of gelatin: negative (6) Cultivation on a litmus milk medium (after incubation at 37° C. for 7 days)

(a) Reaction: BCP blued, litmus changed to bluish violet (b) Coagulation or liquefaction: negative (C) Physiological properties:

(a) Reduction of nitrate: negative (b) Denitrification: negative (c) MR test: negative (d) VP test: negative (e) Formation of indole: negative (f) Formation of hydrogen sulfide: positive (W)

(g) Hydrolysis of starch: negative (h) Utilization of citric acid: positive (i) Utilization of inorganic nitrogen source: only ammonia nitrogen utilized (j) Formation of coloring material: soluble greenish yellow fluorescent pigment (k) Urease: negative (l) Oxidase: positive (m) Catalase: positive (n) Range for growth: pH value of from 5 to 9.5, temperature of from 10° to 43° C.

(o) Oxygen requirement: aerobic (p) O-F test: oxidative (q) Formation of acid or gas from saccharides:

|  | Acid | Gas |
|---|---|---|
| (1) L-Arabinose | + | − |
| (2) D-Xylose | + | − |
| (3) D-Glucose | + | − |
| (4) D-Mannose | + | − |
| (5) D-Fructose | − | − |
| (6) D-Galactose | + | − |
| (7) Maltose | − | − |
| (8) Sucrose | − | − |
| (9) Lactose | − | − |
| (10) Trehalose | − | − |
| (11) D-Sorbit | − | − |
| (12) D-Mannit | − | − |
| (13) Inosit | − | − |
| (14) Glycerin | − | − |
| (15) Starch | − | − |

(r) Arginine dihydrolase: positive (s) Utilization of carbon sources (after incubation at 37° C. for 1 to 7 days): Carbon sources utilized: D-glucose, L-valine, β-L-alanine and L-arginine Carbon sources not utilized: trehalose, meso-inositol and geraniol When this strain is identified with reference to Bergey's Manual of Determinative Bacteriology, 8th edition (1974), it is seen that the strain has characteristics of the genus Pseudomonas.

Since poly-β-hydroxybutyrate is not accumulated in cells, a fluorescent dyestuff is formed and arginine dihydrolase is present, it is seen that the strain belongs to any of the species *Pseudomonas aeroginosa Pseudomonas putida, Pseudomonas fluorescens, Pseudomonas chloraphis* and *Pseudomonas aureofaciens.*

The growth temperature range is higher than that of *P. putida* and closer to that of *P. aeroginosa*. However, since the strain does not reduce a nitrate, does not utilize geraniol, inositol or trehalose but utilizes valine and β-alanine, the strain is determined as a variety of *Pseudomonas putida.*

The typical strain, *Pseudomonas putida* TS-15001, was already deposited at the Fermentation Research Institute, Agency of Industrial Science and Technology, Ministry of International Trade and Industry Japan (Accession No: FERM BP No. 159).

An ordinary nutrient medium containing a carbon source, a nitrogen source, an organic nutrient source and an inorganic nutrient source can be used for culturing the above-mentioned microorganisms.

As the carbon source, there can be mentioned carbohydrates such as glucose, sucrose and molasses, and organic acids and their salts such as tartaric acid, fumaric acid, maleic acid and malic acid. As the nitrogen source, there may be used compounds customarily used for ordinary fermentation, for example, inorganic nitrogen compounds, such as ammonium sulfate, ammonium chloride, ammonia, ammonium phosphate and ammonium nitrate, and organic nitrogen compounds such as urea, corn steep liquor, casein, peptone, yeast extract and meat extract.

As the inorganic nutrient source, there can be used, for example, calcium salts, magnesium salts, potassium salts, phosphates, iron salts, manganese salts, zinc salts and copper salts.

Culturing of the above-mentioned microorganism is carried out according to customary procedures. Ordinarily, culturing is carried out at a temperature of about 20° to about 40° C., preferably about 25° to about 38° C., at a pH value of about 5 to about 9, preferably about 5.5 to about 7.5, aerobically by means of a shaken or submerged culture. Incidentally, if a small amount of an α-APE or a lower alkyl ester of phenylalanine is incorporated in the culture medium, the α-APE-producing activity of the obtained culture of the microorganism or the treated culture thereof can be enhanced.

By the "culture of the microorganism" and the "treated culture product thereof" used herein are meant a liquid culture obtained by culturing a microorganism belonging to the above-mentioned genus, cells collected from this liquid culture, washed cells, dried cells or pulverized cells, obtained by treating the culture or recovered cell, digested cells obtained by autolysis, a product of the cells obtained by means of, for example, an ultrasonic treatment, and bacteriolytic and immobilized products thereof. Moreover, an enzymatic protein fraction obtained from such culture is included.

The separation of cells from the liquid culture and the treatment of the separated cells can easily be accomplished according to customary procedures.

According to the present invention, the above-mentioned culture of the microorganism or the treated culture product thereof may be contacted with fumaric acid, ammonia and a lower alkyl ester of L-phenylalanine in an aqueous solution. The present invention may also be carried out by incorporating fumaric acid, ammonia and a lower alkyl ester of L-phenylalanine into the culture medium in the midway of the culturing, and continuing the culturing, whereby the culture product of the microorganism is contacted with the added compounds.

Fumaric acid, ammonia and L-phenylalanine lower alkyl ester used in the present invention may be in the free state or they may be used in the form of salts. The amount of ammonia is about 0.5 to about 10 equivalents, preferably about 1 to about 5 equivalents, to fumaric acid. Practically, use of both the starting compounds in the form of a salt of both the compounds, that is, ammonium fumarate (ammonium hydrogenfumarate or diammonium fumarate), is advantageous.

The concentrations of fumaric acid, ammonia and the lower alkyl ester of L-phenylalanine at the time of the contact with the culture of the microorganism or the treated culture product thereof are not particularly limited, but each of these concentrations is ordinarily in the range of from about 1% by weight to the solubility limit and preferably in the range of from about 5% by weight to about 40% by weight.

The amount of the culture of the microorganism or the treated culture product thereof used is not particularly limited, but ordinarily, the culture of the microorganism or the treated product thereof is used ordinarily in an amount of about 10 to about 1000 g of wet cells, preferably about 50 to about 500 g of wet cells, based on the molarity of the substrate which is present in the lower concentration.

The reaction temperature may be in the range of from about 10 to about 50° C., preferably about 25° to about 40° C., and the pH value of the liquid reaction mixture may be in the range of from about 4 to about 7, preferably about 5 to about 6. For this adjustment, a buffering agent, an acid or a base may be added to the culture medium.

The reaction time is not particularly critical, but it is ordinarily preferable that the reaction be conducted from about 1 to about 40 hours, especially for about 10 to about 20 hours.

As the lower alkyl group in the lower alkyl ester of L-phenylalanine used in the present invention, there can be mentioned methyl, ethyl and isopropyl groups. D-isomer of the lower alkyl ester of phenylalanine is not used in the present invention, but since the D-isomer does not participate in the reaction, a racemic mixture may be used instead of the L-isomer.

The formed α-APE can be separated and purified according to known separating and purifying means. For example, when the liquid reaction mixture contains solids such as cells, the solids are separated by centrifugal separation or filtration, and if necessary, a protein-removing treatment is carried out and the α-APE is purified and isolated by conventional separating and purifying means such as column chromatography, thin layer chromatography, crystallization or drying under reduced pressure.

According to the present invention, fumaric acid which is obtained more easily and advantageously than L-aspartic acid or N-protected aspartic acid can be used, and an α-APE can directly be obtained.

Furthermore, since the biochemical reaction is utilized, even if a racemic mixture is used as the starting material, the L-isomer of α-APE can be prepared selectively. Moreover, β-APE is not formed as a by-product.

The present invention will now be described in detail with reference to the following examples. In these examples, all of "%" are by weight.

EXAMPLE 1

A mini-jar type fermentation tank having a capacity of 2 liters was charged with 1.0 l of a culture medium (having a pH value of 5.5) comprising 2% of ammonium hydrogenfumarate, 0.1% of monopotassium dihydrogenphosphate, 0.1% of dipotassium monohydrogenphosphate, 0.05% of magnesium sulfate heptahydrate, 0.01% of ferric sulfate heptahydrate, 0.01% of manganese chloride and 0.01% of sodium chloride, with the balance being water, and sterilization was carried out at 120° C. for 15 minutes.

This culture medium was inoculated with 50 ml of a liquid preculture obtained by culturing Psuedomonas putida TS-15001 in a culture medium (having a pH value of 5.5) having the same composition as described above at 37° C. for 16 hours. Culturing was carried out under stirring and aeration at a temperature of 37° C., a stirrer rotation number of 500 rpm and an aeration rate of 1 liter of air per minute while adding an aqueous 2N-HCl solution and an aqueous 2N-NaOH solution so that the pH value was maintained in a range of 5.5 to 6.0 during the culturing period.

After culturing was conducted for 16 hours, a part (500 ml) of the obtained liquid culture was subjected to centrifugal separation to collect 5 g of wet cells. The collected cells were suspended in 25 ml of a 1/50M phosphate buffer solution (having a pH value of 5.5). The suspension was incorporated in 25 ml of an aqueous solution containing 3.3 g of ammonium hydrogenfumarate and 4.5 g of a methyl ester of L-phenylalanine and the mixture was maintained at 37° C. for 16 hours under shaking to effect the reaction.

After completion of the reaction, the liquid reaction mixture was subjected to centrifugal separation at 15° C. and 10,000 rpm for 30 minutes to remove the cells. The obtained supernatant was fractionated by column chromatography (utilizing a column packed with a packing marketed under the tradename of "Toyo Pearl 55F" supplied by Toyo Soda Manufacturing Co., Ltd.) using water/ethanol (80/20 volume ratio) as an eluting solution. A fraction containing an α-L-aspartyl-L-phenylalanine methyl ester was concentrated under reduced pressure to obtain 50 mg of a white powder. The elementary analysis results and physicochemical properties of the powder were as follows.

Elementary analysis (%):

|  | Found | Calculated as α-L-aspartyl-L-phenylalanine methyl ester |
| --- | --- | --- |
| C | 57.70 | 57.14 |
| H | 6.20 | 6.12 |
| N | 10.05 | 9.52 |

Melting point:
235° to 236° (decomposition)
Specific rotatory power:
$[\alpha]25\ D+32.0$ (c=1.0, acetic acid)

The molecular weight of a product obtained by trifluoroacetylating the amino group and methylating the carboxyl group was 404.

The above-mentioned powdery product was subjected to thin layer chromatography, high-speed liquid chromatography and analysis utilizing an amino acid analyzer by using L-phenylalanyl-L-phenylalanine, a methyl ester of L-phenylalanyl-L-phenylalanine, diketopiperazine, L-phenylalanine, L-aspartic acid, L-aspartyl-L-phenylalanine, L-aspartyl-L-aspartic acid, α-L-aspartyl-L-phenylalanine methyl ester and β-L-aspartyl-L-phenylalanine methyl ester as reference substances. Furthermore, a product obtained by methylation of the above powder by hydrochloric acid-methanol and a product obtained by trifluoroacetylation of the above powder by methyl trifluoroacetate were subjected to gas chromatography analysis and gas chromatography/mass spectrography analysis. From the results of these analyses, the above-mentioned powdery product was identified as a methyl ester of α-L-aspartyl-L-phenylalanine.

EXAMPLE 2

In a culture medium having the same composition as that of the culture medium used in Example 1, *Pseudomonas putida* TS-15001 was cultured under the same conditions as those adopted in Example 1. A part (500 ml) of the culture liquid was subjected to centrifugal separation to collect 5 g of wet cells, and the cells were suspended in 25 ml of a 1/50M phosphate buffer solution. The cell suspension was subjected to an ultrasonic vibration treatment at 5° C. for 15 minutes to effect the lysis of the cells. The lytic cell suspension was subjected to centrifugal separation at 5° C. and 10,000 rpm for 15 minutes. The obtained supernatant was incorporated in 25 ml of an aqueous solution containing 3.0 g of ammonium hydrogenfumarate and 4.5 g of a methyl ester of L-phenylalanine and the mixture was maintained at 37° C. under shaking for 16 hours.

The post treatments were conducted in the same manner as described in Example 1, to obtain 30 mg of an L-aspartyl-L-phenylalanine methyl ester in the form of a white powder.

We claim:

1. A process for preparing an aspartylphenylalanine alkyl ester comprising the steps of:
   (1) contacting a substrate comprising fumaric acid, ammonia and an L-phenylalanine lower alkyl ester each present in an amount of at least about 1% by weight to saturation, with a liquid culture, cells or a lytic product of cells of a microorganism having the identifying characteristics of *Pseudomonas putida*, TS-15001 (FERM BP 159), and which is capable of producing an α-L-aspartyl-L-phenylalanine lower alkyl ester, in which the concentration of the cells or the treated product thereof is in the range of about 10 to about 1,000 g of wet cells based on the molarity of the substrate which is present in the lowest concentration, said contacting being at a temperature in the range of about 10° C. to about 50° C., at a pH in the range of about 4 to about 7, for a period of time sufficient to prepare the desired aspartylphenylalanine ester, and thereafter
   (2) recovering the α-L-aspartyl-L-phenylalanine lower alkyl ester from the reaction mixture.

2. A process according to claim 1, wherein the culture of the microorganism is cells of the microorganism.

3. A process according to claim 1, wherein the treated culture product of the microorganism is a bacteriolytic product of the microorganism.

4. A process according to claim 1 wherein the lower alkyl group of each of the L-phenylalanine lower alkyl ester and the α-L-aspartyl-L-phenylalanine lower alkyl ester is a methyl group.

5. The process of claim 1, wherein the step (1) is conducted at a temperature in the range of about 25° C. to about 40° C.

6. The process of claim 1, wherein the pH of step (1) is in the range of from about 5 to about 6.

7. The process of claim 1, wherein the concentration of each of the fumaric acid, ammonia and the L-phenylalanine lower alkyl ester is in the range of from about 5% by weight to about 40% by weight.

8. The process of claim 1, wherein the amount of cells used in step (1) is in the range of about 50 g to about 500 g.

9. The process of claim 1, wherein the reaction of step (1) is conducted for a period of from 1 hour to about 40 hours.

10. The process of claim 9, wherein the reaction of step (1) is conducted for a period of from about 10 hours to about 20 hours.

11. The process of claim 1, wherein a lytic cell suspension of *Pseudomonas putida* is used.

12. The process of claim 1, wherein the microorganism is *Pseudomonas putida* TS-15001(FERM BP 159).

* * * * *